United States Patent [19]

Maguire et al.

[11] Patent Number: 5,086,232
[45] Date of Patent: Feb. 4, 1992

[54] METHODS OF AND APPARATUS FOR INSPECTING SURFACES FOR DEFECTS

[75] Inventors: Sean P. J. Maguire, Barwell; Kandiah Sivayoganathan, Beeston; Velupillai Balendran, Moseley, all of United Kingdom

[73] Assignee: Jaguar Cars Limited, England

[21] Appl. No.: 547,467

[22] Filed: Jun. 29, 1990

[30] Foreign Application Priority Data

Jun. 30, 1989 [GB] United Kingdom ............... 8915093
Sep. 8, 1989 [GB] United Kingdom ............... 8920358

[51] Int. Cl.$^5$ ............................................. G01N 21/88
[52] U.S. Cl. ..................................... 250/572; 356/376
[58] Field of Search ............... 250/571, 572, 562; 356/237, 430, 431, 376

[56] References Cited

U.S. PATENT DOCUMENTS

| | | | |
|---|---|---|---|
| 4,306,813 | 12/1981 | Sick ........................... | 250/572 |
| 4,759,074 | 7/1988 | Iadipaolo et al. . | |
| 4,966,455 | 10/1990 | Avni et al. ................. | 250/571 |
| 4,966,457 | 10/1990 | Hayano ...................... | 250/572 |

FOREIGN PATENT DOCUMENTS

| | | |
|---|---|---|
| 53-057087 | 7/1978 | Japan . |
| 58-204350 | 3/1984 | Japan . |
| 2133871 | 12/1982 | United Kingdom . |
| 2159271 | 11/1985 | United Kingdom . |
| 89/07235 | 8/1989 | World Int. Prop. O. . |

OTHER PUBLICATIONS

GM Scrutinizes Body Surfaces, Automotive News OEM edition, Jan. 9, 1989, Vision 3D, brochure.
S. S. Hupp and T. B. Hackett of Ashland Chemical, Quantitative Analysis of Surface Quality for Exterior Body Panels, Feb. 29–Mar. 4, 1988, Loria Surface Analyzer System, brochure.

*Primary Examiner*—David C. Nelms
*Assistant Examiner*—K. Shami
*Attorney, Agent, or Firm*—Davis, Bujold & Streck

[57] ABSTRACT

A method of inspecting a surface of a member such as a motor vehicle body panel includes the steps of setting up the member at an inspection site, directing light on to the surface at a high angle of incidence so as to form a transverse trace across the surface and to reflect light from the surface with a low angle of deflection to form an image of the trace on a detection screen. A record of the image is produced. The trace is also viewed and recorded directly from a position substantially perpendicular to the surface. The records of the image and of the trace are analysed together to give an indication of the nature of the surface at the trace. The light is scanned in relation to the member to form further transverse traces across the member and the new traces and images are also analysed.

8 Claims, 2 Drawing Sheets

METHODS OF AND APPARATUS FOR INSPECTING SURFACES FOR DEFECTS

BACKGROUND TO THE INVENTION

The invention relates to a method of inspecting surfaces of members for defects.

Members such as motor car body panels which are produced in large numbers may include some members or panels with defects. With steel body panels local defects such as surface pitting can occur but also on pressing of the panels, some may be manufactured with a defective shape.

In a finished motor car the most prominent way in which defects show up is in irregular distortion of reflections from a high-gloss finish. Regular distortion is of course to be expected due to the curvature of a panel.

It has already been proposed in the LORIA (Trade Mark) surface analyser system of Ashland Chemicals to analyse or inspect the surface of a panel by reflecting a laser beam from a panel onto a screen at a high angle of incidence to give a low angle of deflection (that is a small deflection from the incident direction) in the beam, scanning the beam across the panel to form a trace, recording the image of the trace on the screen, similarly producing traces, images and records for successive parts of the panel, and analysing the records of the images to give a measure of the shape and surface quality of the panel. The present invention is concerned with an improvement to a system of this kind.

The known system can be effective for detecting some surfaces with small degrees of curvature and small irregularities but some kinds of contour of the panel can not be detected effectively and accurately.

An objective of the present invention is to provide an improved system in which the above disadvantages are reduced or overcome.

SUMMARY OF THE INVENTION

In accordance with the present invention there is provided a method of inspecting a surface of a member including the steps of setting up the member at an inspection site, directing light on to the surface at a high angle of incidence so as to form a trace thereacross and to reflect light from the surface with a low angle of deflection (that is a small deflection from the incident direction) to form an image of the trace on a detection screen, producing a record of the shape of the image, viewing and producing a record of the shape of the trace of light on the surface from a position substantially perpendicular thereto, analysing the record of the image and the record of the trace together to give an indication of the nature of the surface at said trace, scanning the light in relation to the member to form further transverse traces across the member and repeating the remaining steps for the new traces.

In addition to the data associated with the geometry of the incident light and the image on the screen, the substantially perpendicular view provides additional data relating to the line of contact of the incident light on the panel. By analysing data from both the reflected image and its trace on the panel together, an improved indication as to the nature of the surface can be established.

Preferably the incident light is generated by a laser and preferably this laser operates within the visible spectrum.

Preferably the incident light forms a trace across the panel by being focused into a fan shaped beam, the cross section of which is a transverse line, but alternatively the trace could be formed by a narrow beam of light, which scans across the panel in a transverse line.

Although a useful degree of analysis of a surface can be carried out by visual inspection and comparison of images and traces, computer analysis results in a very powerful tool. Data representing the shape of the panel may be analysed by deriving that bivariate third order polynomial which gives the best possible fit with the data and employing error signals between the polynomial and the actual data as a measure of the acceptability of the surface. The computerised system is then appropriate for automatic or semi-automatic inspection techniques enabling it to reject or accept individual panels. In the context of motor vehicle body panels, this kind of inspection technique can improve the quality of a motor car body.

The system is useful for flat or nearly flat car body panels including for example door skins and boot and bonnet lids. For more deeply shaped parts such as typical wing panels, the technique can not normally be applied because the extreme curvature of such panels renders them unsuitable for scanning the whole surface. It might be possible to test relatively flat parts of these very curved panels but results are unlikely to be sufficiently valuable to warrant the expense.

BRIEF DESCRIPTION OF THE DRAWINGS

An embodiment of the invention will now be described with reference to the accompanying drawings in which.

DESCRIPTION OF A PREFERRED EMBODIMENT

Figure 1:
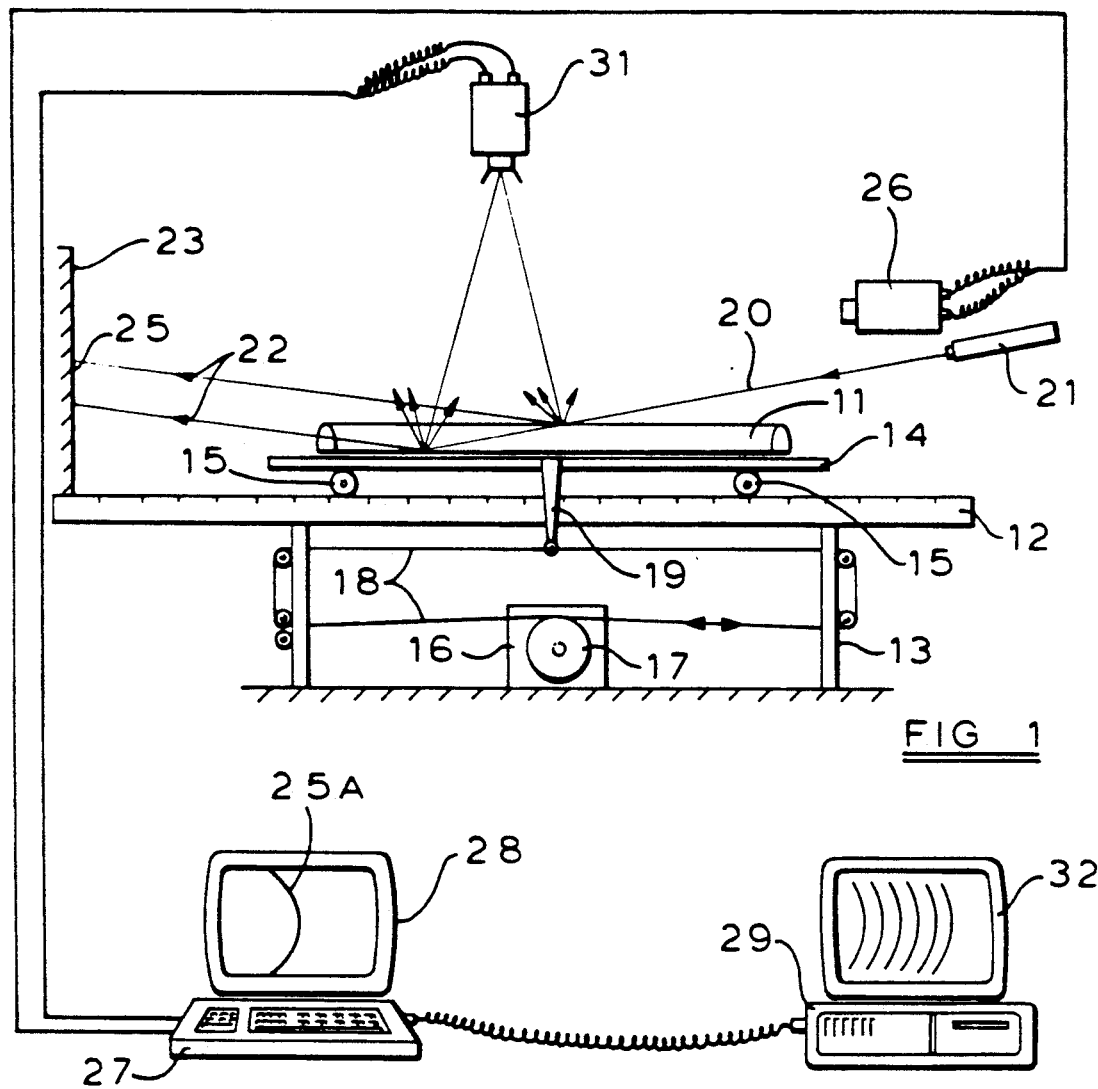
FIG. 1 is a diagramatic layout drawing of a complete apparatus for performing the invention.
Figure 2:
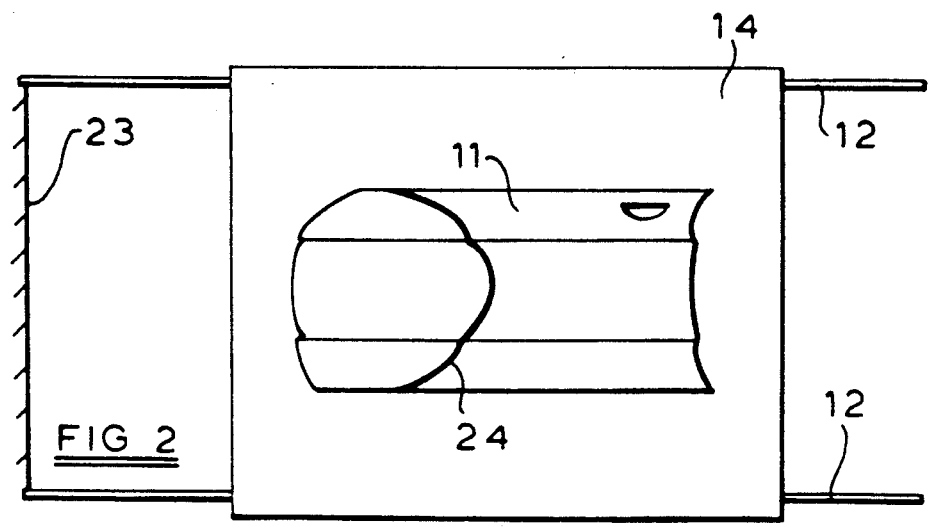
FIG. 2 is a plan view showing part of the arrangement for FIG. 1.

FIG. 1 illustrates an installation for carrying out a method of inspecting the surface of a member 11 for defects. In this example the member 11 is a door panel for a motor vehicle body in a condition known in the industry as "body in white" or "BIW". This is a sheet steel pressing to which no paint or other surface coating has been applied. It may be necessary in some cases to coat the surface with a reflective material to achieve a sufficiently clear reflection. The method could however be used for inspecting other types of surface such as painted surfaces or surfaces of plastics mouldings or of glass fibre reinforced plastics.

The apparatus comprises a horizontal bed 12 on a supporting structure 13. A table 14 is mounted on the bed 12, runs along the table on rollers 15 and is accurately constrained so that it moves only linearly.

A stepper motor unit 16 drives a pulley 17 which in turn drives the table 14 via a cable 18 and drive bracket 19. In use, the body panel is mounted positively on the table 14 and thus it can be indexed in steps or moved continuously in the longitudinal direction of the bed 12.

A source of coherent visible light, for example, a 5 mW He Ne laser 21 is mounted in a fixed position such that its output is directed at the panel with a high angle of incidence so as to produce reflected light with a low angle of deflection, that is with a small deflection from its incident direction. An incident angle of the order of 85° giving a deflection of about 10° is suitable. There is a requirement for the laser beam to impinge on the whole width to be inspected. This may be achieved by a narrow beam focused to a single point and traversed across the surface of the panel but preferably the laser output is focused into a fan shaped planar beam 20 so that at any instant it impinges on the whole width to be inspected. For narrow panels of 20 or 30 cm width, the whole width of the panel is inspected in one pass. For wider door panels, the panel may be inspected in several separate passes to cover its whole width.

Figure 3:
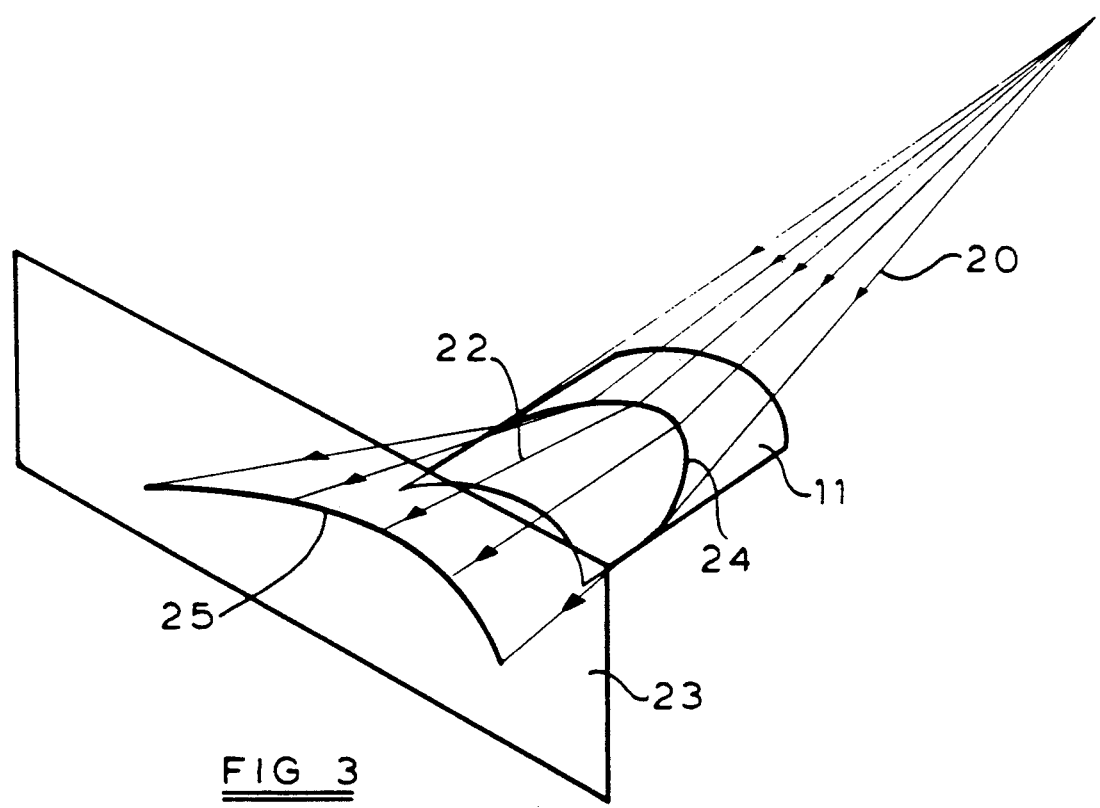
FIG. 3 illustrates the formation of an image on a screen in the arrangement of FIGS. 1 and 2.

A significant portion of the light is reflected as from a mirror as indicated by arrows 22 and forms an image on a screen 23 arranged substantially perpendicular to the longitudinal direction of the bed 12 and the direction of the incident light from laser 21. If the surface of the panel is not sufficiently reflective in itself it should be made more reflective by means of a suitable coating. The generation of the image is best illustrated in FIG. 3. The flat fan shaped incident beam 20 is shown to impinge on the panel 11, forming a trace 24 on the panel. The shape of this trace is curved due to the curvature of the body panel and the curvature of the actual trace 24 is amplified due to the high angle of incidence. The directly reflected light 22 then impinges on screen 23 to form the shape of an image 25. The shape of the image 25 conforms generally to the cross-sectional shape of the panel but its curvature is magnified by the divergence of the beam and is distorted (in this example elongated) by outward deflection due to the curvature of the panel.

FIG.1 shows a first camera 26 directed at the screen 23 to record the shape of the image 25 formed on the screen. The camera is connected to a vision system 27 which displays the image as 25A on a monitor 28. Signals or data representing a record of the image 25 are also transmitted to a computer 29 for analysis.

A second camera 31 is arranged directly above the panel 11 and is directed at the region where the laser beam impinges on the panel to form the trace 24. Some of the light incident on the trace is scattered rather than being reflected with the result that the trace is visible from various angles and can be recorded by camera 31. The output from camera 31 representing the shape of the trace 24 is fed to a vision system, in this example the same vision system as used for camera 26. The trace may be displayed on screen 28 if required. Signals or data representing a record of the trace are transferred to computer 29.

The incident light beam of necessity has a significant depth with the result that the trace 24 and image 25 have significant depth. For accurate resolution an edge of the trace or image is defined by the position at which a threshold light level is achieved. The definitive line of the trace or image may be taken as one of these edges or the mean position of the two edges.

In use, the table 14 carrying the panel 11 is stepped in increments of a few millimeters along the bed 12. In this way, the laser beam is effectively indexed along the panel. An image 25 and trace 24 are recorded for each indexed position, building up a family of traces and images. By way of example, a series of such images are shown on the monitor 32 of computer 29. As an alternative the panel could move continuously, traces and images being recorded at specific intervals.

In this way, a series of images and traces representing the transverse curvature of the panel may be viewed simultaneously, facilitating judgement as to the quality of the panel.

The data collected during scanning of the panel gives a complete representation of its shape and this shape is analysed in the computer in the following way. A simplified representation of the actual measured shape is derived in the form of that bivariate third order polynomial which gives the best possible fit between the actual surface and the derived polynomial. For a regularly curved panel, the bivariate third order polynomial will fit reasonaly closely to the actual panel but for an irregularly curved panel there will be substantial differences or errors between the polynomial and the actual shape.

These error signals may be displayed as colour signals superimposed on a family of curves such as shown on screen 32, with different colours representing different ranges of magnitude. An operator may inspect the colour coded display and accept or reject a panel on the basis of a subjective judgement of the significant presence of colours representing large error signals. Alternatively, panels could be rejected automatically on the basis of a particular level of error signal.

With the inspection and analysis just described, irregularities in the surface are detected but the panel is not compared with a standard reference panel. Comparison with a standard panel may be achieved by other means or may not be necessary.

With an alternative analysis procedure, the computer may be loaded with a bivariate third order polynomial which defines an ideal shape for the surface. Rather than calculating this polynomial, it could be derived by inspection of a series of panels known to be of the required shape and averaging the signals derived therefrom.

The signals representing a family of images and traces from a panel being inspected would then be compared with and fitted to the standard polynomial in such a way as to effectively position the panel in register with the ideal shape. Error signals representing the departure of the actual surface from the ideal are derived. These may be displayed as before or used for automatic acceptance or rejection.

Although processing of the image 25 alone can produce useful results and similarly processing of traces 24 as recorded in camera 31 can likewise give useful results, combining the information from the image 25 and the trace 24 gives a more effective indication of the nature of the surface.

The data from the two cameras is complementary as will now be explained.

The data recorded by the first camera 31 completely fixes the position in space of a point on the panel, but with low resolution. In particular, the point is known to lie in the fixed plane of the incident light and its position along and across this plane is recorded by camera 31 which observes a view substantially perpendicular to this plane. However the resolution is not good because the plane of the light and the surface being detected are at very shallow angles with respect to each other leading to a line of intersection which is not sharply defined.

The data recorded in the second camera from the image is in itself ambiguous in that it represents a combination of panel position and panel angle; the same image point on the screen could be achieved by reflections at different angles from different positions in the plane of the incident light. However the screen is substantially perpendicular to the reflected light giving a sharper high resolution image.

By combining data from the low resolution accurate position trace and the high resolution ambiguous positive image, a particularly clear definition of the panel can be achieved.

We claim:

1. A method of inspecting a surface of a member including the steps of setting up the member at an inspection site, directing light on to the surface at a high angle of incidence so as to form a transverse trace there across and to reflect light from the surface with a low angle of deflection to form an image of the trace on a detection screen, producing a record of the shape of the image, viewing and producing a record of the shape of the trace of light on the surface from a position substantially perpendicular thereto, analyzing the record of the image and the record of the trace together to give an indication of the nature of the surface at said trace, scanning the light in relation to the member to form further transverse traces across the member and repeating the viewing, recording and analysis steps for the new traces.

2. A method as claimed in claim 1 wherein the light source is a laser.

3. A method as claimed in claim 1 in which the light is focused in to a fan shaped planar beam to form the trace across the surface.

4. A method as claimed in claim 3 wherein one edge of the trace or image representing an edge of the beam is recorded as representative of the trace or image.

5. A method as claimed in claim 1 wherein data representing the shape of the panel is analysed by deriving that bivariate third order polynomial which gives the best possible fit with the data and employing error signals between the polynomial and the actual data as a measure of the acceptability of the surface.

6. A method as claimed in claim 1 wherein signals representative of the actual shape of the surface of the member are derived from the image and trace signals and are compared with previously recorded data representing an ideal shape to provide error signals indicative of defects.

7. A method as claimed in claim 6 wherein the errors are displayed in ranges of magnitude.

8. Apparatus for carrying out the method as claimed in claim 1 including a table for supporting a member, a source of light set to be incident on the table at a high angle of incidence, a screen arranged to receive an image reflected from the surface of the member, means for recording the form of the image, means for viewing the trace of the beam on the member from a position substantially perpendicular to the member and means for deriving signals indicative of the shape of the member from the received image and trace signals.

* * * * *